United States Patent [19]

Pershin et al.

[11] 4,016,289
[45] Apr. 5, 1977

[54] MEDICINAL PREPARATION FOR TREATMENT OF VIRAL-ETIOLOGY DISEASES

[76] Inventors: Grigory Nikolaevich Pershin, Novopeschanaya ulitsa, 19/10, kv. 75; Nadezhda Sergeevna Bogdanova, ulitsa 26 Bakinskikh Komissarov, 1, korpus 1, kv. 26; Irina Sergeevna Nikolaeva, Matveevskaya ulitsa, 1, kv. 179; Jury Fedorovich Maichuk, ulitsa Usievicha, 11, kv. 4; Roza Isaakovna Abramishvili, ulitsa Narodnogo opolchenia, 11, kv. 27; Teshabai Nazarovich Avazov, Sadovo-Chernogryazskaya ulitsa, 14/19, kv. 1; Galina Yakovlevna Uretskaya, Belyaevo-Bogorodskoe, kvartal 46-47, korpus 40, kv. 170; Svetlana Jurievna Anikina, B. Serpukhovskaya ulitsa, 70, kv. 5; Alexei Nikolaevich Grinev, Belyaevo-Bogorodskoe, kvartal 44, korpus 9, kv. 57; Maxim Yakovlevich Kraft, Leninsky prospekt, 93, kv. 29, all of Moscow, U.S.S.R.

[22] Filed: May 27, 1975

[21] Appl. No.: 581,413

Related U.S. Application Data

[63] Continuation of Ser. No. 224,271, Feb. 7, 1972, abandoned.

[52] U.S. Cl. .............................. 424/315; 424/331; 424/333
[51] Int. Cl.[2] .............. A61K 31/185; A61K 31/11; A61K 31/12
[58] Field of Search .................. 424/333, 315, 331

[56] References Cited

OTHER PUBLICATIONS

Chem. Abst. – 8th Coll. Index, vol. 66–75, 1967–1971, pp. 32839S & 32840S.

*Primary Examiner*—Sam Rosen

[57] ABSTRACT

A medicinal preparation for treatment of viral-etiology diseases contains the bisulphite compound of 2-fluorenonyl-glyoxal in combination with a pharmaceutical vehicle or unctuous base.

A method of producing the bisulphite compound of 2-fluorenonyl-glyoxal, viz, the active principle of said medicinal preparation, consists in that fluorene is acylated by dichloroacetyl chloride in the presence of aluminum chloride and phosphoryl chloride in an organic solvent, the resultant 2-ω-dichloroacetylfluorene is oxidized by the salts of chromic acid in an acetic-acid medium at 50°–90° C into 2-ω-dichloroacetylfluorenone which is made to interact with morpholine at 50°–98° C to form 2-ω-dimorpholinoacetylflourenone, or otherwise, fluorenone is acylated by acetic anhydride in an organic solvent in the presence of aluminum chloride, the resultant 2-acetylfluorene is oxidized by chromic acid or by the salts thereof in an acetic acid medium at 50°–90° C to obtain 2-acetylfluorenone which is brominated in an organic solvent at 60°–110° C, the resultant 2-ω-dibromoacetylfluorenone is reacted with morpholine at 50°–98° C to form 2-ω-dimorpholinoacetylfluorenone the latter is hydrolyzed by dilute mineral acids at 20°–100° C into 2-fluorenonyl-glyoxal hydrate which is then made to react with sodium bisulphite in an aqueous-alcohol medium at 60°–80° C to isolate the final product.

15 Claims, No Drawings

MEDICINAL PREPARATION FOR TREATMENT OF VIRAL-ETIOLOGY DISEASES

This application is a continuation application of Ser. No. 224,271, Feb. 7, 1972 now abandoned.

The present invention is concerned with a novel medicinal preparation used in treatment of viral-etiology diseases.

According to the invention, said new preparation contains the active principle, viz, the bisulphite compound of 2-fluorenonyl-glyoxal in combination with a pharmaceutical menstruum or vehicle, or unctuous excipient.

The herein-proposed preparation provisionally called by us "florenal", due to is antiviral effect, is applicable for treatment of virus diseases of the eye, skin and in acute virus-caused respiratory infections.

The principal indications for the application of the present preparation are: superficial herpetic keratitis; stromal herpetic keratitis and keratouveitis caused by the virus of herpes simplex; keratitis and keratouveitis caused by the virus of herpes zoster; adenoviral conjunctivitis; epidemic adenoviral keratoconjunctivitis; skin lesions caused by the virus of herpes simplex and that of herpes zoster; skin lesions caused by other viruses; prophylaxis and treatment of influenza and of some other acute virus-caused respiratory diseases.

The field of application of the preparation depends upon its ability to suppress the reproduction of the virus of herpes, of influenza and of some other viruses.

When tested in experiments on tissue culture the preparation manifests more pronounced inhibitory activity against the virus of herpes vulgaris than many other preparations (tebrophen, oxoline) do, and is not inferior to idoxuridine (5-iodo-$2^1$-desoxyuridine).

The preparation which is essentially the bisulphite compound of 2-fluorenonyl-glyoxal, possesses high antivirulent activity against the virus of influenza when under experiment on tissue culture and on chick embryos.

When applied in experiments on mice that have been intracerebrally infected with the virus of herpes, the preparation renders a definite protective effect, thus safeguarding from death up to 61–76 percent of animals, whereas in the blank test the percentage of the survived animals proves to be as low as 35.

Application of a 0.25–1-percent ointment of the preparation for treating an experimentally caused herpetic keratitis due to the virus of herpes, renders a pronounced therapeutic effect not inferior to that of idoxuridine and superior to that produced by desoxyribonuclease and tebrophen.

The preparation has been tested clinically for treatment of 213 patients suffering from virus diseases of the eye, out of whom 143 patients have been afflicted by the viral-infection herpes, 61 patients, by the adenoviral herpes and by other eye diseases, nine patients. The viral nature of the disease has been corroborated by the detection of the viral antigen in scraped matter or by serological examination of the fresh serum.

In treatment of 143 patients suffering from various forms of the viral-infection herpes, a positive therapeutic effect has been observed in 125 patients or 80.4 percent.

In treatment of superficial herpetic keratites (dendriform, vesicular, marginal) the preparation proved to manifest the highest therapeutic effect, viz, out of 80 patients 74 have been cured (92.5 percent). Subjective amelioration occurs as a rule within the initial days of treatment, while objective diminishing of infiltration and evidences of epitelization are observed after 2–4 days of treatment. Duration of treatment until a complete epitelization of the cornea in the case of dendriform keratitis equals 16.1 days and in mappy keratitis, 13.5 days. Clinical recovery is accompanied by favorable results with respect to vision.

A good therapeutic effect of the preparation has also been found in treating deep herpetic keratites and keratouveites, the majority of patients having been unsuccessfully treated with other preparations (idoxuridine, desoxyribonuclease, gamma-globulin, interferon) beforehand. Out of 63 patients to whom the preparation was administered 49 (77.7 percent) have been cured. As to other patients in whom the course of the disease has been found especially grave, the administration of the preparation either has been combined with the application of other medicaments or cancelled altogether.

As compared to other methods of treatment the number of recurrent cases of herpetic keratitis diminishes. Thus, in one of the groups, wherein treatment has been conducted by the present preparation, the recurrence of the disease has been observed in nine patients out of 50 subjected to examination within the post-recovery period from 13 months to 2.5 years.

In case of a concomitant bacterial infection, antiviral treatment has been combined with the application of antibacterial means.

In case of adenoviral conjunctivitis (caused by adenoviruses of the serotypes 3 and 7) and epidemic keratoconjunctivitis (caused by adenoviruses of the serotype 8), the preparation has been administered to 61 patients. A positive therapeutic effect has been observed in 60 patients (98.3 percent), while in one patient the preparation has been substituted by another one due to its inadequate effectiveness. As a result of the drug administration, the amelioration of the conditions of the eyes has been observed as early as after 2–3 days of treatment. Duration of treatment until complete abatement of all conjunctival phenomena and ensuing of clinical recovery, takes 6 to 15 days, 10.9 days on the average.

The preparation has also turned out to be effective in treating virus skin diseases caused by the virus of herpes simplex, herpes zoster and by some other viruses.

The preparation may be used both under stationary and ambulant therapy conditions.

According to the invention, the medicinal preparations for treatment of viral-etiology diseases, incorporates the active principle, viz, the bisulfite compound of 2-fluorenonyl-glyoxal in combination with a pharmaceutical vehicle or unctuous base.

According to the invention, the medicinal preparation contains distilled water or a polyvinyl alcohol (ethenol) solution as a pharmaceutical vehicle. It is preferable to use a 2.5-percent solution of polyvinyl alcohol (ethenol) as a pharmaceutical vehicle.

It is expedient to use the medicinal preparation containing the active principle in an amount of 0.1 to 1 percent.

According to the invention, the medicinal preparation contains vaseline or (petroleum jelly) or anhydrous lanolin. It is expedient to prepare an ointment with the weight percentage of the active principle equal to 0.25–0.5.

For treatment of herpetic keratites, both superficial and stromal (of lighter form), it is expedient to put a 0.25-percent ointment of the preparation into the conjunctival sac 3–5 times daily or instillate a 0.1-percent aqueous solution of the preparation 5 times a day or 0.1-percent polymer solution of the preparation 3 times a day.

For treatment of stromal herpetic keratitis, herpetic keratouveitis and keratouveitis caused by the virus of herpes zoster, it is recommended that a 0.5-percent ointment of the preparation be put thrice a day or a 0.1-percent aqueous or polymer solution of the preparation be instilled 5 times a day.

For treating viral lesions of the skin it is recommended to apply a 0.5-percent ointment of the preparation to the affected skin area thrice a day.

For prophylaxis or treatment of influenza and acute respiratory infections, it is recommended to smear the nasal passages with a 0.5-percent ointment of the preparation twice a day or introduce a 0.25 -percent aqueous or polymer solution of the preparation into the nose thrice a day.

In some cases an ointment or solution of the preparation may cause burning sensation of the mucosa of the eye, which ceases after 5–10 minutes. In case of eyelid irritation, the preparation must be cancelled or its dosage be reduced. Irritation of the mucosa is more frequently caused by a 0.5-percent ointment of the preparation as compared to a 0.25-percent ointment and by a 0.25-percent solution as compared to a 0.1-percent solution. A polymer solution of the preparation is better tolerated by the mucosa of the eye than an aqueous solution or ointment thereof.

No absolute counterindications for the applications of the preparation occur. In treating grave forms of herpetic keratites should no therapeutic effect be observed within 10 days, an additional or another treatment must be precribed for the patient.

The ointment of the preparation is to be stored in cold place, packed in aluminum tubes varnished on the inside, or in well stoppered glass jars; the preparation refers to List B as per the USSR Pharmacopeia and must be stored with precaution. No change of the preparation is found after it has been under one-year storage.

The present invention resides also in a method of producing the active principle of the proposed preparation, viz, the bisulfite compound of 2-fluorenonyl-glyoxal.

Known in the present-day practice is a method of producing the bisulfite compound of 2-fluorenonyl-glyoxal, said method consisting in that fluorene is acylated by acetic anhydride in the presence of aluminum chloride to obtain 2-acetylfluorene at a yield of 60 weight percent. Then the thus-obtained 2-acetylfluorene is oxidized by sodium bichromate in an acetic-acid medium at 70°–75° C during 6 hours and 2-acetylfluorenon is isolated at a yield of 50 weight percent.

The thus-isolated 2-acetylfluorenon is oxidized by selenium dioxide in dioxane medium at 98°–100° C during 22 hours to obtain 2-fluorenonyl-glyoxal isolated as semiacetal, the yield being equal to 31.2 weight percent. The thus-obtained intermediate product is subjected to treatment with sodium bisulfite in 60-percent ethanol to obtain the final product crystallizable with a molecule of water. The yield of the final product amounts to 57 weight percent when calculated for the semiacetal of 2-fluorenonyl-glyoxal and to 55 weight percent when calculated for the parent fluorene (of.-Sintez organicheskikh preparatov/synthesis of organic preparations/, v.4, P.77, 1953 /in Russian/; Zhurnal organicheskoy khimii /Journal of organic chemistry/, 33, 3053, 1963 (in Russian).

The disadvantages of the aforesaid method are low yield and low quality of the final product, as well as the use of a highly toxic substance viz, selenium dioxide in the process.

It is an essential object of the present invention to increase the yield of the final product, dispense with the use of highly toxic substances and obtain high-quality final product suitable for medical uses.

Said object is accomplished due to the provision of a method for producing the bisulfite compound of 2-fluorenonyl-glyoxal, wherein according to the invention, fluorene is acylated by dischloroacetyl chloride in the presence of aluminum chloride and phosphoryl chloride in an organic solvent, the resultant 2-ω-dichloroacetylfluorene is oxidized by the salts of chromic acid in an acetic-acid medium at 50°–90° C to obtain 2-ω-dichloroacetylfluorenone which is made to react with morpholine at 50°–98° C to form 2-ω-dimorpholinoacetylfluorenone, or alternatively, fluorene is acylated by acetic anhydride in an organic solvent in the presence of aluminum chloride, the thus obtained 2-acetylfluorene is oxidized by chromic acid or by the salts thereof in an acetic acid medium at 50°–90° C to obtain 2-acetylfluorenone which is brominated in an organic solvent at 60°–100° C to form 2-ω-dibromoacetylfluorenone, the latter is made to react with morpholine at 50°–98° C to form 2-ω-dimorpholinoacetylfluorenone which is hydrolyzed by dilute mineral acids at 20°–100° C to obtain 2-fluorenonyl-glyoxal hydrate, the latter reacting with sodium bisulfite in an aqueous-alcohol medium at 60°–80° C to isolate the final product.

It is expedient to use benzene chloride as the organic solvent in the acylation process.

It is preferable for the acylation process of fluorene by dichloroacetyl chloride to run at 10°–15° C at the initial stage and at 30°–40° C at the terminal stage thereof.

The process of fluorene acylation by acetic anhydride is expedient to occur at 18°–20° C at the beginning stage and at 40°–50° C during the final stage thereof. The oxidation process is preferable to run at 80°–90° C.

The oxidation process is expedient to be carried out with the use of sodium bichromate.

It is preferable to employ acetic acid or chloroform as the organic solvent in the bromination process and that the latter be carried out under exposure to light. To increase the yield, the reaction of the aforesaid products with morpholine is expedient to occur at 40°–50° C.

It is preferable to run the process of hydrolysis at 55°–60° C.

It is most favorable that an aqueous solution of hydrochloric or sulfuric acid be used as dilute mineral acids.

Aqueous ethanol is favorable to be used as the aqueous alcohol.

The herein-proposed method is carried into effect as follows.

As a starting material use is made of fluorene which is acylated by dichloroacetyl chloride in the medium of an organic solvent, preferably in the medium of chlorobenzene, in the presence of catalysts, viz, aluminum chloride and phosphoryl chloride. It is advantageous that the process be initiated at a temperature of 10°–15° C followed by gradually heating to 30°–40° C during 1 hour. The process results in obtaining 2-ω-dichloroacetylfluorene in a yield of 78–82 weight percent. The thus-obtained product is oxidized by the salts of chromic acid, e.g., by sodium bichromate in an acetic acid medium at 50°–90° C, preferably at 80°–90° C, within 3–4 hours, whereupon 2-ω-dichloroacetylfluorenone is isolated in a yield of 65–69 weight percent as calculated for 2-ω-dichloroacetylfluorene, or up to 53.4–56.5 weight percent when calculated for the initial fluorene.

The thus-obtained 2-ω-dichloroacetylfluorenone is heated with morpholine at 50°–98° C, preferably at 40°–50° C to obtain 2-ω-bismorpholinoacetylfluorenone in a yield of 11–87 weight percent as calculated for 2-ω-dichloroacetylfluorene, or 6.2–49 weight percent when calculated for fluorene.

Further, the resultant 2-ω-bismorpholinoacetylfluorenone is subjected to hydrolysis by dilute mineral acids, e.g., hydrochloric or sulfuric at 20°–100° C, preferably at 55°–60° C to obtain 2-fluorenonyl-glyoxal hydrate in a yield of 93–100 weight percent as calculated for 2-ω-dimorpholinoacetylfluorenone, or 45.5–49 weight percent when calculated for fluorene. The thus-obtained 2-fluorenonyl-glyoxal hydrate is treated with sodium bisulfite in the medium of aqueous alcohol, preferably aqueous ethanol at 60°–80° C to isolate the final product. The yield of the final product amounts to 88 weight percent as calculated for 2-fluorenonyl-glyoxal hydrate, or 42.2 weight percent when calculated for fluorene.

The process may also occur in the following way.

Fluorene is acylated by acetic anhydride in an organic solvent, e.g., chlorobenzene in the presence of aluminum chloride at 18°–20° C at the initial stage of the process followed by heating to 40°–50° C to obtain 2-acetylfluorene at a yield of up to 74 weight percent. The latter is oxidized by chromic acid or by the salts thereof in an acetic acid medium at 50°–90° C for 4–12 hours to obtain 2-acetylfluorenone in a yield of 27–68 weight percent as calculated for 2-acetylfluorene, or 20–50 weight percent when calculated for fluorene. The resultant product is brominated in an organic solvent, e.g., chloroform at 50°–60° C or in acetic acid at 100°–110° C. The yield of the thus-formed 2-ω-dibromoacetylfluorenon equals 71–88 weight percent as calculated for 2-acetylfluorenone, or 35.4–44 weight percent when calculated for fluorene. Then 2-ω-dibromoacetylfluorenone is made to react with morpholine when heated to 50°–98° C for 1–2 hours to obtain 2-ω-bismorpholinoacetylfluorenone in a yield of 40–85 weight percent as calculated for 2-ω-dibromoacetylfluorenone, or 17.6–37.4 weight percent when calculated for fluorene.

Further, the process runs in a way similar to that described above. The yield of the final product equals 30–35 weight percent as calculated for fluorene.

The herein-proposed method makes it possible to dispense with toxic substances and obtain a high-quality final product suitable for medical uses.

One more advantage of the method proposed herein is a 6.1–7.9 fold increase in the yield of the final product as compared to the method known heretofore.

To promote understanding, given below are the following examples of carrying into effect the method of producing the bisulfite compound of 2-fluorenonyl-glyoxal.

EXAMPLE 1

Into a solution of 83.0 g (0.5 mol) of fluorene in 375 ml of chlorobenzene (distilled) and 40 ml (84.0 g; 0.05 mol) of phosphoryl chloride, are introduced 142.5 g (1.07 mol) of aluminum chloride at 10°–15° C and under vigorous stirring, whereupon 73.8 g (0.5 mol) of dichloroacetyl chloride are gradually added thereto. After the addition the resultant mixture is heated to 30°–40° C for 1 hour, and then poured into 615 g of ice and 24 ml of concentrated hydrochloric acid. Just after that chlorobenzene in the form of an azeotropic mixture with water is distilled off under vacuum from the reaction mixture. The resultant precipitate is filtered off from the oleiferous product, washed with 250–300 ml of methanol and air-dried. The yield equals 113.0 g (82 weight percent), m.p. 136.5°–137.5° C (from glacial acetic acid).

Found (wt.%): C 64.77; H 3.41; Cl 25.20. $C_{15}H_{10}Cl_2O$. Calculated (wt.%): C 65.01; H 3.64; Cl 25.58.

Further, to the solution of 113.0 g (0.41 mol) of 2-ω-dichloroacetylfluorene in 1130 ml of glacial acetic acid are added 368 g of sodium bichromate at 80° C with vigorous stirring, and the reaction mixture is allowed to stand for 4 hours at 80° C. Then the mixture is poured into 22 l of water heated to 90° C and the resultant mixture is cooled down to room temperature. The precipitate is filtered off, washed on the filter with 585 ml of 2-percent sulfuric acid and with water. Thereupon, the precipitate is treated, while under good stirring, with 265 ml of a 5-percent caustic soda solution at 50° C, refiltered, washed with water and recrystallized from glacial acetic acid. The yield of the resultant 2-ω-dichloroacetylfluorenone equals 82.0 g (69 weight percent as calculated for 2-ω-dichloroacetylfluorene or 56.5 weight percent when calculated for fluorene); m.p. 193°–195° C.

Found (wt.%): C 62.13; H 2.90; Cl 24.53. $C_{15}H_8Cl_2O_2$ Calculated (wt.%): C 61.88; H 2.77; Cl 24.35.

A mixture of 82.0 g (0.28 mol) of 2-ω-dichloroacetylfluorenone and 414 ml (4.75 mol) of anhydrous morpholine is heated within 4 hours at 40°–50° C, stirred, cooled down to room temperature and allowed to stand overnight in a cooler. Then, the precipitate is filtered off, washed with 70 ml of morpholine and carefully intermixed with 1.1 l of water, then refiltered and washed on the filter with 85 ml of methanol. The yield of 2-ω-dimorpholinoacetylfluorenone is equal to 95.0 g (87 weight percent as calculated for 2-ω-dichloroacetylfluorenone or 49 weight percent when calculated for fluorene), m.p. 138°–140° C (with decomposition from dioxane).

Found (wt.%): C 70.34; H 5.91; N 7.02. $C_{23}H_{24}N_2O_4$. Calculated (wt.%): C 70.39; H 6.17; N 7.14.

Further, 160 ml of hydrochloric acid (1.1) are added dropwise to a suspension of 95.0 g (0.24 mol) of 2-ω-dimorpholinoacetylfluorenone in 320 ml of water while being cooled with ice and under stirring, whereupon the mixture is heated to 60° C during 10 min, then cooled down to room temperature. The precipitate is filtered off, washed with water until the acid reaction disappears.

The yield of the resultant 2-fluorenonyl-glyoxal hydrate equals 60.0 g (98.0 weight percent as calculated for 2-dimorpholinoacetylfluorenone or 48 weight percent when calculated for fluorene). M.p. 196°–198° C. M.p. 198°–200° C (with decomposition from glacial acetic acid).

Found (wt.%): C 71.14; H 3.81. $C_{15}H_{10}O_4$. Calculated (wt.%): C 70.86; H 3.97.

To the hot solution of 60.0 g (0.24 mol) of 2-fluorenonyl-glyoxal hydrate in 1.09 ml of a 60-percent ethanol are added 66.5 ml (0.086 kg; 0.37 mol) of a 48 percent aqueous solution of sodium bisulfite and the mixture is allowed to stand overnight at room temperature. The resultant precipitate is filtered off, washed with 155 ml of 96-percent ethanol and 155 ml of acetone.

The yield of the final product equals 74.5 g (88 weight percent as calculated for 2-fluorenonyl-glyoxal hydrate or 42.2 weight percent when calculated for fluorene).

Found (wt.%): C 50.49; H 3.23; S 8.74. $C_{15}H_9O_6$-$SNa.H_2O$. Calculated (wt.%): C 50.28; H 3.10; S 8.95.

EXAMPLE 2

Into a solution of 83.0 g (0.5 mol) of fluorene in 375 ml of chloro benzene (distilled) are introduced 134. g (1;01 mol) of aluminum chloride at room temperature and under vigorous stirring, whereupon 52.0 ml (57.0 g; 0.26 mol) of acetic anhydride are added dropwise thereto at such a rate that the temperature of the reaction mixture does not rise above 50° C within 1 hour). Then the mixture is stirred for another 3 hours at 50° C, cooled down to room temperature and poured under stirring into 600 g of ice and 30 ml of concentrated hydrochloric acid. After that, chloro benzene in the form of an azeotropic mixture with water, is distilled off under vacuum from the resultant mixture. When the distillation is complete, the resultant precipitate is filtered off, washed with water until the acid reaction disappears and air-dried. Then the precipitate is boiled with 790 ml of isopropanol with the addition of some activated charcoal (10.0 g). The hot mixture is filtered off and allowed to stand overnight at room temperature. The resultant precipitate is filtered off, washed with 50 ml of isopropanol and air-dried. The yield of 2-acetylfluorene is equal to 77.0 g (74 weight percent as calculated for fluorene), m.p. 129°–131° C.

To a solution of 77.0 g (0.74 mol) of 2-acetylfluorene in 1.1 l of acetic acid are added at 90° C and under intense stirring, 385 g (1.3 mol) of sodium bichromate during a period of 1 hr to 1 hr 15 min. Thereupon, the reaction mixture is allowed to stand under the same conditions for 4 hours, then poured into 4.6 l of water heated to 90° C and kept overnight at room temperature. The precipitate is filtered off, washed with 900 ml of a 2-percent sulfuric acid till a colorless wash solution appears, and with water until the acid reaction disappears. Then the precipitate is treated under intense stirring, with 540 ml of a 5-percent caustic soda solution heated to 90° C, and let cool down to room temperature. The precipitate is filtered off, washed with water and dried in a drying cabinet at 80° C to obtain 62.5 g of crude 2-acetylfluorenone which is then recrystallized from 1.0 l of benzene for the sake of purity. The yield of 2-acetylfluorenone equals 55.5 g (68.0 wt% as calculated for 2-acetylfluorene or 50 wt.% when calculated for fluorene), m.p. 160°–161.5° C.

To a boiling solution of 55.5 g (0.25 mol) of 2-acetylfluorenone in 740 ml of chloroform are added dropwise 30.0 ml (96.0 g; 0.6 mol) of bromine during 2 hours at such a rate that the entire amount of bromine would have enough time to react. The process runs on exposure to light. Then the mixture is let stand for 3.5–4 hours until bromine ceases to evolve, whereupon it is cooled down to room temperature. The resultant precipitate is filtered off, washed with 135 ml of chloroform. The yield of 2-ω-dibromoacetylfluorenone equals 83.0 g (88 wt.% as calculated for 2-acetylfluorenone or 44.0 wt.% when calculated for fluorene); m.p. 209°–211° C. For analysis, the product is recrystallized from glacial acetic acid; m.p. 211°–212° C.

Found (wt.%): C 47.12; H 2.20; Br 41.99. $C_{15}H_8Br_2O_2$. Calculated (wt.%): C 47.41; H 2.13; Br 42.04.

A mixture of 83.0 g (0.22 mol) of 2-ω-dibromoacetylfluorenone and 250 ml (2.9 mol) of morpholine is heated under stirring during 1 hour at 50°–60° C over a water bath, then cooled down to 18°–20° C and let stand for 1–2 hours in an ice-cooled bath. The resultant precipitate is filtered off and mixed with 140 ml of methanol, then refiltered, washed with 70 ml of methanol and mixed with 420 ml of water. Then the precipitate is filtered off again and washed with water until the halogen disappears (Beilstein test), and air-dried. The yield of 2-ω-dimorpholinoacetylfluorenone equals 73.5 g (85 wt.% as calculated for 2-ω-dibromoacetylfluorenon or 37.4 wt.% when calculated for fluorene), m.p. 137°–139° C (upon mixture test with the sample obtained in Example 1, the melting point shows no depression).

From 73.5 g (0.19 mol) of 2-ω-dimorpholinoacetylfluorenone in a way similar to that described in Example 1, are obtained 47.6 g of 2-fluorenonyl-glyoxal hydrate (100 wt.% as calculated for 2-ω-dimorpholinoacetylfluorenone or 37.4 wt.% when calculated for fluorene).

From 47.6 g (0.19 mol) of 2-fluorenonyl-glyoxal hydrate in a way similar to that described in Example 1, are obtained 60.5 g of the final product (84 wt.% as calculated for 2-fluorenonyl-glyoxal hydrate or 33.2 wt.% when calculated for fluorene).

EXAMPLE 3

From 83 g of fluorene in a way similar to that described in Example 2, are obtained 77 g (74 wt.% of 2-acetylfluorene as calculated for fluorene.

To a solution of 77 g of 2-acetylfluorene in 1.1 l of acetic acid are added at 50° C and under intense stirring, 385 g of sodium bichromate. The mixture is heated at the same temperature under stirring for 12 hours. Further, the mixture is treated in the same way as described in Example 2. The yield of 2-acetylfluorenone equals 22.4 g (27 wt.% as calculated for 2-acetylfluorene or 19.8 wt.% when calculated for fluorene), m.p. 157°–159° C. From 22.4 g of 2-acetylfluorenone in a way similar to that described in Example 2, are obtained 33.5 g of 2-ω-dibromoacetylfluorenone (88 wt.% as calculated for 2-acetylfluorenone or 7.4 wt.% when calculated for fluorene).

From 33.5 g of 2-ω-dibromoacetylfluorenone in a way similar to that described in Example 2, are obtained 29.7 g of 2-ω-dimorpholinoacetylfluorenone (85 wt.% as calculated for 2-ω-dibromoacetylfluorenone or 14.7 wt.% when calculated for fluorene). From 29.7 g of 2-ω-dimorpholinoacetylfluorenone in a way similar to that described in Example 1 are obtained 19.3 g of 2-fluorenonyl-glyoxal hydrate (100 wt.% as calculated for 2-ω-dimorpholinoacetylfluorenone or 14.7 wt.% when calculated for fluorene).

From 19.3 g of 2-fluorenonyl-glyoxal hydrate in a way similar to that described in Example 2, are obtained 24.4 g of the final product (84 wt.% as calculated for 2-fluorenonyl-glyoxal hydrate or 12.3 wt.% when calculated for fluorene).

EXAMPLE 4

From 83.0 g of fluorene, 2-acetylfluorene is produced in a way similar to that described in Example 2, the yield being 77.0 g (74 wt.% as calculated for fluorene).

From 77 g of 2-acetylfluorene in a way similar to that described in Example 2, are obtained 55.5 g of 2-acetylfluorenone (68 wt.% as calculated for 2-acetylfluorene or 50 wt.% when calculated for fluorene).

To a boiling solution of 55.5 g (0.25 mol) of 2-acetylfluorenone in 1000 ml of glacial acetic acid, at 100°–110° C, under stirring and on exposure to light, are added dropwise 35 ml (112 g, 0.74 mol) of a solution of bromine in 65 ml of glacial acetic acid at such a rate that the whole amount of bromine would have enough time to react.

Then the mixture is allowed to stand at 100° C for 4 hours and let stay overnight at room temperature. Thereupon, the resultant precipitate is filtered off and treated in a way similar to that described in Example 1 to obtain 2-ω-dibromoacetylfluorenone in an amount of 79.9 g (77 wt.% as calculated for 2-acetylfluorenone or 36.3 wt.% when calculated for fluorene); m.p. 207°–209° C.

From 79.9 g of 2-ω-dibromoacetylfluorenone in a way similar to that described in Example 2, are obtained 70.2 g of 2-ω-dimorpholinoacetylfluorenone (85 wt.% as calculated for 2-ω-dibromoacetylfluorenone or 31 wt.% when calculated for fluorene). From 70.2 g of 2-ω-dimorpholinoacetylfluorenone in a way similar to that described in Example 1 are obtained 45.6 g of 2-fluorenonyl-glyoxal hydrate (100 wt.% as calculated for 2-ω-dimorpholinoacetylfluorenon or 31 wt.% when calculated for fluorene). From 45.6 g of 2-fluorenonyl-glyoxal hydrate in a way similar to that described in Example 1, are obtained 57.5 g of the final product (84 wt.% as calculated for 2-fluorenonyl-glyoxal hydrate or 26 wt.% when calculated for fluorene),

EXAMPLE 5

The process of obtaining 2-ω-dibromoacetylfluorenone is similar to that described in Example 2. fluorenone (88 wt.% as calculated for 2-acetylfluorenone or 44 wt.% when calculated for fluorene).

A mixture of 83 g of 2-ω-dibromoacetylfluorenone and 460 ml of morpholine is stirred at 98° C for 2 hours and treated as described in Example 2 to obtain 34.6 g of 2-ω-dimorpholinofluorenone (40 wt.% as calculated for 2-ω-dibromoacetylfluorenon or 17.6 wt.% when calculated for fluorene; m.p. 133°–135° C (with decomposition).

From 34.6 g of 2-ω-dimorpholinoacetylfluorenone in a way similar to that described in Example 1, are obtained 22.5 g of 2-fluorenonyl-glyoxal hydrate (100 wt.% as calculated for 2-ω-dimorpholinoacetylfluorenone or 17.6 wt.% when calculated for fluorene). From 22.5 g of 2-fluorenonyl-glyoxal hydrate in a way similar to that described in Example 2, are obtained 28.5 g of the final product (84 wt.% as calculated for 2-fluorenonyl-glyoxal hydrate or 14.8 wt.% when calculated for fluorene).

EXAMPLE 6

The production procedure of 2-ω-dichloroacetylfluorenone is carried out similar to that described in Example 1 to obtain 82 g of 2-ω-dichloroacetylfluorenone (64 wt.% as calculated for 2-ω-dichloroacetylfluorene or 56.5 wt.%, when calculated for fluorene).

A mixture of 82.0 g of 2-ω-dichloroacetylfluorenone and 414 ml of anhydrous morpholine is heated for 2.5 hours at 95° C, then treated as described in Example 1 to obtain 12.2 g of 2-ω-dimorpholinoacetylfluorenone (11.2 wt.% as calculated for 2-ω-dichloroacetylfluorenon or 6.2 wt.% when calculated for fluorene; m.p. 135°–136° C (with decomposition).

From 12.2 g of 2-ω-dimorpholinoacetylfluorenone in a way similar to that described in Example 1, are obtained 7.95 g of 2-fluorenonyl-glyoxal hydrate (100 wt.% as calculated for 2-ω-morpholinoacetylfluorenone or 6.2 wt.% when calculated for fluorene). From 7.95 g of 2-fluorenonyl-glyoxal hydrate in a way similar to that described in Example 1, are obtained 9.8 g of the final product (84 wt.% as calculated for 2-fluorenonyl-glyoxal hydrate or 5.85 wt.% when calculated for fluorene).

EXAMPLE 7

The production process of 2-ω-dimorpholinoacetylfluorenone is carried out similar to that described in Example 2 to obtain 73.5 g of 2-ω-dimorpholinoacetylfluorenone (85 wt.% as calculated for 2-ω-dibromoacetylfluorenone or 37.4 wt.% when calculated for fluorene).

To a suspension of 74.5 g of 2-ω-dimorpholinoacetylfluorenone in 245 ml of water are added dropwise 245 ml of 20-percent sulfuric acid with ice-cooling and stirring, whereupon the mixture is heated to 60° C during 10 min., then treated in a way similar to that described in Example 1 to obtain 47.8 g of 2-fluorenonyl-glyoxal hydrate (100 wt.% as calculated for 2-ω-dimorpholinoacetylfluorenone or 37.4 wt.% when calculated for fluorene); m.p. 191°–193° C (with decomposition).

From 47.8 g of 2-fluorenonyl-glyoxal hydrate in a way similar to that described in Example 2, are obtained 60.7 g of the final product (84 wt.% as calculated for 2-fluorenonyl-glyoxal hydrate or 33.2 wt.% when calculated for fluorene).

EXAMPLE 8

The production procedure of 2-ω-dimorpholinoacetylfluorenone occurs as described in Example 2 to obtain 73.5 g of 2-ω-dimorpholinoacetylfluorenone (85 wt.% as calculated for 2-ω-dibromoacetylfluorenone or 37.4 wt.% when calculated for fluorene.

A suspension of 73.5 g of 2-ω-dimorpholinoacetylfluorenone in 380 ml of hydrochloric acid (1:1) is heated at 100° C under stirring within 1–2 min., then treated as described in Example 1 to obtain 47 g of 2-fluorenone-glyoxal hydrate (98.5 wt.% as calculated for 2-ω-dimorpholinoacetylfluorenone or 36.8 wt.% when calculated for fluorene), m.p. 194°–195° C (with decomposition).

From 47 g of 2-fluorenonyl-glyoxal hydrate in a way similar to that described in Example 2, are obtained 59.9 g of the final product (84 wt.% as calculated for 2-fluorenonyl-glyoxal hydrate or 31 wt.% when calculated for fluorene).

EXAMPLE 9

The production procedure of 2-ω-dimorpholinoacetylfluorenone occurs as described in Example 1 to obtain 95 g of 2-ω-dimorpholinoacetylfluorenone (87 wt.% as calculated for 2-ω-dichloroacetylfluorenone or 48 wt.% when calculated for fluorene). A mixture of 95.0 g of 2-ω-dimorpholinoacetylfluorenone and 475 ml of hydrochloric acid (1:1) is allowed to stand for 2 days. Then the mixture is treated in a way similar to that described in Example 7 to obtain 61.5 g of 2-fluorenonyl-glyoxal hydrate (100 wt.% as calculated for 2-ω-dimorpholinoacetylfluorenone or 49 wt.% when calculated for fluorene); m.p. 192°–194° C (with decomposition).

From 61.5 g of 2-fluorenonyl-glyoxal hydrate in a way similar to that described in Example 2, is obtained the final product in an amount of 72.9 (84 wt.% as calculated for 2-fluorenonyl-glyoxal hydrate or 41 wt.% when calculated for fluorene).

What we claim is:

1. A medicinal preparation for the treatment of virus-caused eye and skin diseases, said preparation containing an amount effective against said virus of the bisulfite compound of 2-fluorenonyl-glyoxal in combination with an unctuous base.

2. A medicinal preparation according to claim 1 wherein the unctuous base is anhydrous lanolin.

3. A medicinal preparation according to claim 1 wherein the unctuous base is Vaseline.

4. A medicinal preparation according to claim 1 wherein the bisulfite compound is present in the amount of 0.25–0.5 weight percent of the composition.

5. A medicinal preparation for the treatment of virus-caused eye and skin diseases, said preparation containing an amount effective against said virus of the bisulfite compound of 2-fluorenonyl-glyoxal in combination with a polyvinyl alcohol solution.

6. A medicinal preparation according to claim 5 wherein the polyvinyl alcohol solution has a concentration of 2.5 percent polyvinyl alcohol.

7. A medicinal preparation according to claim 5 wherein the bisulfite compound is present in the amount of 0.1 to 1.0 weight percent of the composition.

8. A method for the treatment of virus-caused eye and skin diseases comprising administering to the affected eye or skin area of the human or animal host afflicted with said disease an amount effective against said virus of a medicinal composition comprising the bisulfite compound of 2-fluorenonyl-glyoxal.

9. A method according to claim 8 wherein the disease is caused by a herpes virus.

10. A method according to claim 8 wherein said bisulfite compound is present in the amount of 0.1 to 1 weight percent of the composition.

11. A method according to claim 8 wherein said bisulfite compound is present in combination with an unctuous base.

12. A method according to claim 8 wherein said bisulfite compound is present in combination with a polyvinyl alcohol solution.

13. A method according to claim 12 wherein said bisulfite compound is present in combination with an unctuous base.

14. A method of treatment of virus-caused influenze comprising applying to the nasal passages of the human or animal host afflicted with said influenze a medicinal preparation comprising the bisulfite compound of 2-fluorenonyl-glyoxal in an amount effective against said virus.

15. A method according to claim 14 wherein said bisulfite compound is present in combination with a polyvinyl alcohol solution.

* * * * *